United States Patent [19]
Takesako et al.

[11] Patent Number: 6,103,767
[45] Date of Patent: Aug. 15, 2000

[54] PHYSIOLOGICALLY ACTIVE SUBSTANCES TKR1785'S, PROCESS FOR THE PREPARATION THEREOF, AND MICROBE

[75] Inventors: Kazutoh Takesako; Naoyuki Awazu; Yoshie Yoshikawa; Eiko Koyama; Ikunoshin Kato, all of Otsu, Japan

[73] Assignee: Takara Shuzo Co., Ltd., Kyoto, Japan

[21] Appl. No.: 09/142,689

[22] PCT Filed: Mar. 12, 1997

[86] PCT No.: PCT/JP97/00770

§ 371 Date: Oct. 29, 1998

§ 102(e) Date: Oct. 29, 1998

[87] PCT Pub. No.: WO97/34012

PCT Pub. Date: Sep. 18, 1997

[30] Foreign Application Priority Data

Mar. 12, 1996 [JP] Japan ................................. 8-084712

[51] Int. Cl.[7] ............................ A01N 37/18; A61K 31/16
[52] U.S. Cl. ......................... 514/616; 514/626; 564/159; 564/160
[58] Field of Search ..................... 514/616, 626; 564/159, 160

[56] References Cited

FOREIGN PATENT DOCUMENTS 2 135 668   9/1984   United Kingdom .

*Primary Examiner*—Dwayne C. Jones
*Attorney, Agent, or Firm*—Pollock, Vande Sande & Amernick

[57] ABSTRACT

The object of the present invention is to provide a novel bioactive substance of value as a therapeutic agent for mycosis, and the like.

This invention relates to the bioactive substance TKR1785 of the following general formula (A):

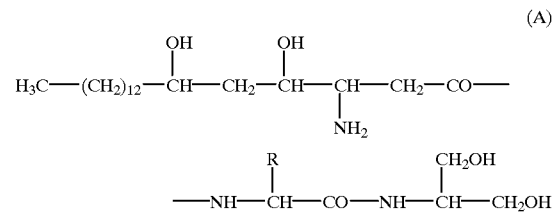

(wherein R represents —CH(CH$_3$)$_2$ or —CH(CH$_3$)C$_2$H$_5$).

7 Claims, 8 Drawing Sheets

PHYSIOLOGICALLY ACTIVE SUBSTANCES TKR1785'S, PROCESS FOR THE PREPARATION THEREOF, AND MICROBE

CROSS-REFERENCES TO RELATED APPLICATIONS

This application is a U.S. national phase application under 35 USC 371 of PCT/JP97/00770 filed Mar. 12, 1997 which in turn claims priority from Japanese Application Hei-8-84712 filed Mar. 12, 1996.

TECHNICAL FIELD

The present invention relates to the bioactive substance TKR1785 which is of value as a therapeutic agent for mycoses, allergic diseases, and immune diseases, a method of producing said bioactive substance, and further a microorganism producing the bioactive substance TKR1785.

BACKGROUND ART

It is known that fungi infect man, animals, and plants to cause various diseases. In man, for instance, some fungi cause superficial mycosis of the skin and mouth cavity, while others cause systemic mycosis of the viscera and brain or the like. Fungi also cause similar infectious diseases in pet animals and livestock. There also are fungi which induce various diseases in crop plants such as orchard trees and vegetables.

Among those pathogenic fungi which cause systemic mycosis in man are fungal species of the genera Candida, Cryptococcus, and Aspergillus. Referring to superficial mycosis, candidal species which infect the skin, mouth cavity, and vagina, trichophytons infecting the skin of the limbs (the causative organisms of athlete's foot), and Malassezia species (the causative organisms of tinea versicolor) are regarded as representative pathogenic fungi. In addition to those fungi, a variety of other fungi also inhabit the earth 's ecology and suspected to do harm to animals and plants.

Recent years have seen a dramatic increase in the incidence of allergic diseases such as asthma, atopic dermatitis, and allergic rhinitis. The pathogenesis of many of those allergic diseases is generally explained as follows. As the host is sensitized by a disease-inducing antigen, an IgE antibody (reagin) specific to antigen, i.e. allergen, is produced in the host's serum and tissues. As the host is reexposed to the allergen, the IgE coupled to the mast cells or basophils and the specific allergen form complexes and the IgE-complex crosslinks on the cell surface, and triggers physiological events arising from IgE-antigen interactions. Substances known as chemical mediators are involved in those physiological events.

Some of them are the chemical mediators preexisting in the granules of mast cells and eosinophils but released extracellularly by degranulation upon activation, such as histamine, serotonin, eosinophilic factors, etc., while others are synthesized de novo by the activation of mast cells. As to the latter mediators, activation of phospholipase $A_2$ entails activation of lipoxigenase and cyclooxigenase which act upon the arachidonic acid derived from the membrane phospholipid to produce various leukotrienes and thromboxanes. Those chemical mediators cause long-term allergic inflammentions such as contraction of bronchial smooth muscle and mucosal edema, or the like. Those events may be either systemic or local according to the route by which the antigen enters into the body and the pattern of deposition of IgE on the mast cells or basophils. The local symptoms generally occur on the surface of the epithelium at the site of entry of the allergen. The systemic event includes anaphylactic shock which is the result of response of the IgE-basophil to the antigen in the vasculature.

There are many allergic diseases in which various substances in the environment, inclusive of ticks and pollens, and antigenic substances contained in foods act as allergens. Among them, allergic diseases caused by fungi are also numerous and allergens derived from fungi of various genera such as Candida, Aspergillus, Alternaria, Cladosporium, Malassezia, and Penicillium act as the etiologic factors.

Few antifungal agents are known today which can be used in the treatment and prevention of those fungal infections and contaminations for which such fungi are responsible. Among those agents, amphotericin B, flucytosine, miconazole, fluconazole, etc. can be mentioned as therapeutic agents for systemic infections in men and animals. However, those substances are not fully satisfactory in efficacy, toxicity, and/or antibacterial spectrum and have not proved sufficiently useful as therapeutic agents.

Meanwhile, there are various kinds of therapeutic agents for allergic diseases, such as lipoxigenase inhibitors which inhibit production of said various chemical mediators, thromboxane synthase inhibitors, antihistaminics which antagonize the chemical mediator, and leukotriene receptor antagonists. In addition, steroids not only inhibit production of chemical mediators but have various physiological activities, thus being the most important of antiallergic agents.

SUMMARY OF THE INVENTION

Under the circumstances, the object of the present invention is to provide a novel bioactive substance of value as a therapeutic agent for mycosis, allergic diseases, and immune diseases.

The inventors of the present invention isolated a large number of microorganisms from the natural kingdom in their exploration of new bioactive substances, screened for the bioactive substances they produced, and studied their biological properties. As a result, they discovered bioactive substances showing antifungal activity against pathogenic fungi such as Candida, Aspergillus, Cryptococcus, Malassezia, etc. in culture broths of a strain of microorganism belonging to the genus Penicillium. Then, the inventors isolated the bioactive substances and investigated their physicochemical properties. As a result, they could establish that the substance actually comprises novel substance having some unique physicochemical properties and named them TKR1785 (hereinafter referred to as TKR1785-I) and TKR1785-II (the two substances will hereinafter be referred to collectively as TKR1785). Furthermore, it was found that TKR1785 not only inhibits the enzymes associated with allergic reactions but also exerts other physiological activities on the immune system. The present invention has been developed on the basis of the above finding.

The present invention, therefore, is directed, in the first aspect, to the novel bioactive substance TKR1785 which is represented by the following general formula (A):

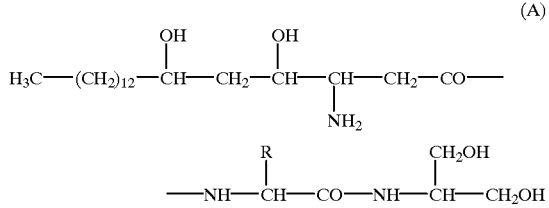

(wherein R represents —CH(CH$_3$)$_2$ or —CH(CH$_3$)C$_2$H$_5$)

The present invention is further directed, in the second aspect, to a method of producing the novel bioactive substance TKR1785 which comprises culturing a strain of microorganism belonging to the genus Penicillium and capable of elaborating said novel bioactive substance TKR1785 and isolating said substance from the resulting culture broth.

In the third aspect, the present invention is directed to a microorganism belonging to the genus Penicillium and capable of producing the bioactive substance TKR1785.

In the fourth aspect, the present invention is directed to a pharmaceutical composition comprising the bioactive substance TKR1785.

DETAILED DESCRIPTION OF THE INVENTION

The bioactive substance TKR1785-I has the following physicochemical characteristics (1), (2), (3), (4), (5), (6), and (7).

Figure 1:
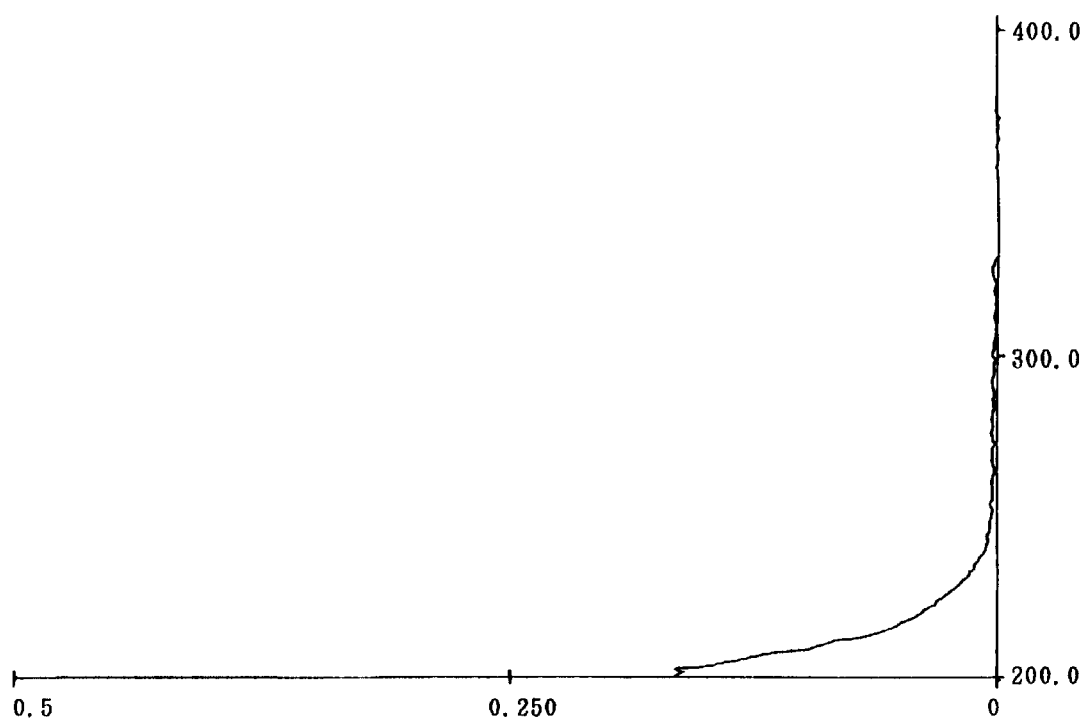
FIG. 1 is an ultraviolet absorption spectrum of the bioactive substance TKR1785-I. The ordinate represents wavelength (nm).

(1) Mass spectrum (FAB-MS): m/z 518 [M+H]$^+$ (2) Molecular formula: C$_{27}$H$_{55}$N$_3$O (3) UV spectrum (in methanol), terminal absorptions as shown in FIG. 1.

(4) IR spectrum (KBr); dominant absorption wavenumbers: 3410 cm$^{-1}$, 2920 cm$^{-1}$, 2850 cm$^{-1}$, 1670 cm$^{-1}$, 1540 cm$^{-1}$, 1470 cm$^{-1}$, 1210 cm$^{-1}$, 1140 cm$^{-1}$, 1050 cm$^{-1}$, 840 cm 800 cm$^{-1}$, 720 cm$^{-1}$.

(5) Soluble in methanol and water, sparingly soluble in chloroform and hexane.

Figure 3:
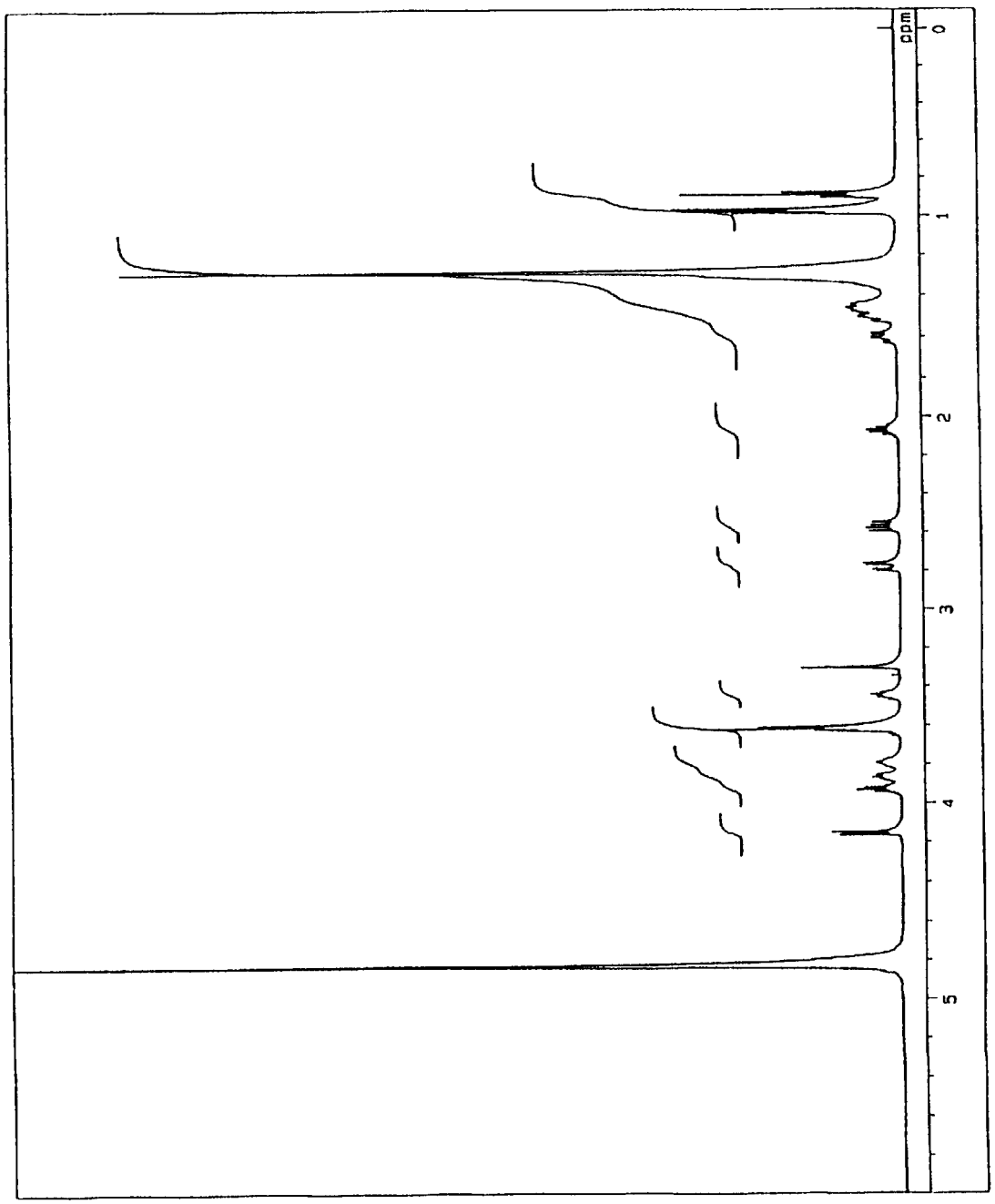
FIG. 3 is an $^1$H-NMR spectrum of the bioactive substance TKR1785-I. The abscissa represents chemical shift (ppm).
Figure 4:
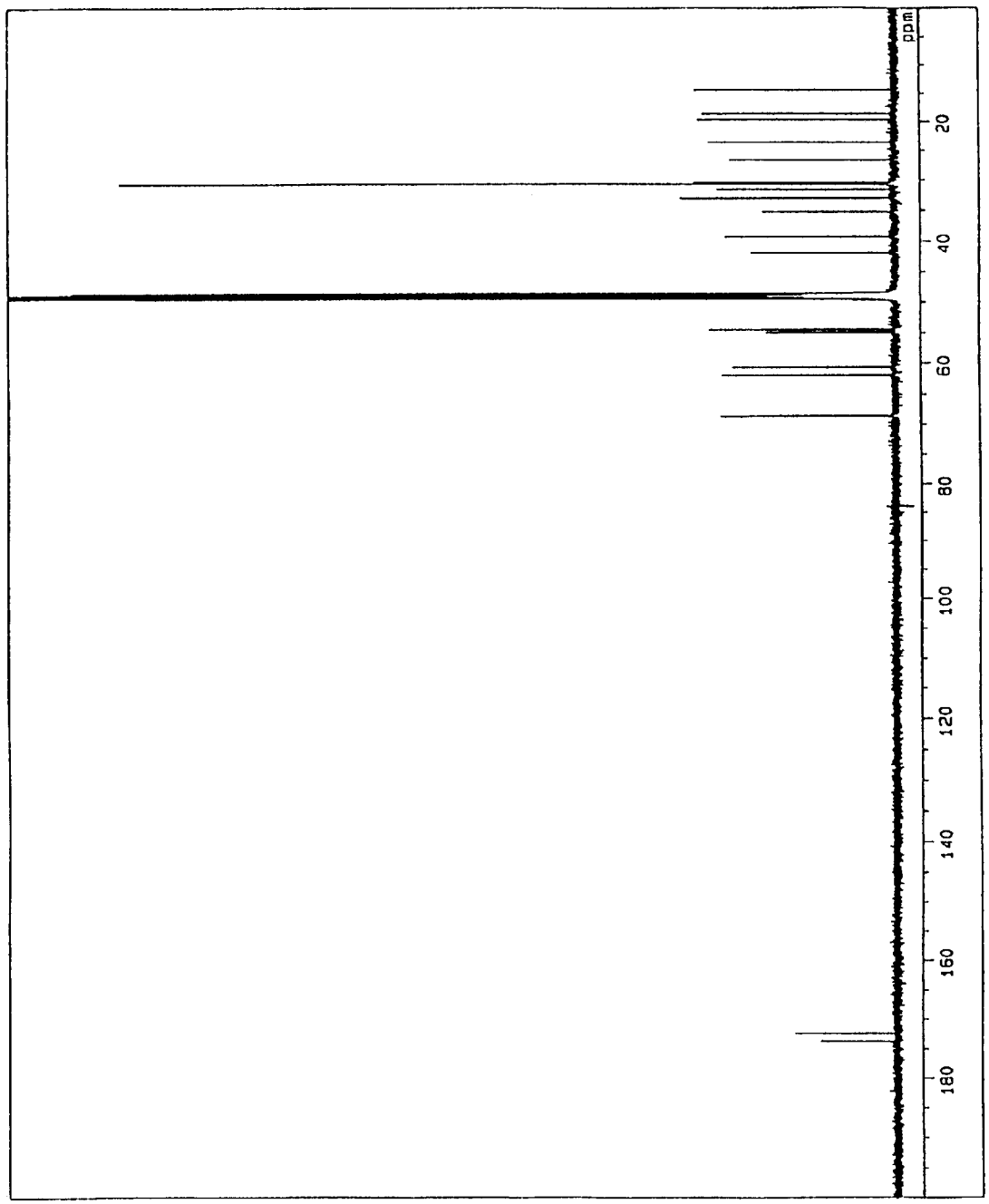
FIG. 4 is a $^{13}$C-NMR spectrum of the bioactive substance TKR1785-I. The abscissa represents chemical shift (ppm).

(6) $^1$H-NMR spectrum: FIG. 3 and C-NMR spectrum: FIG. 4.

Figure 5:
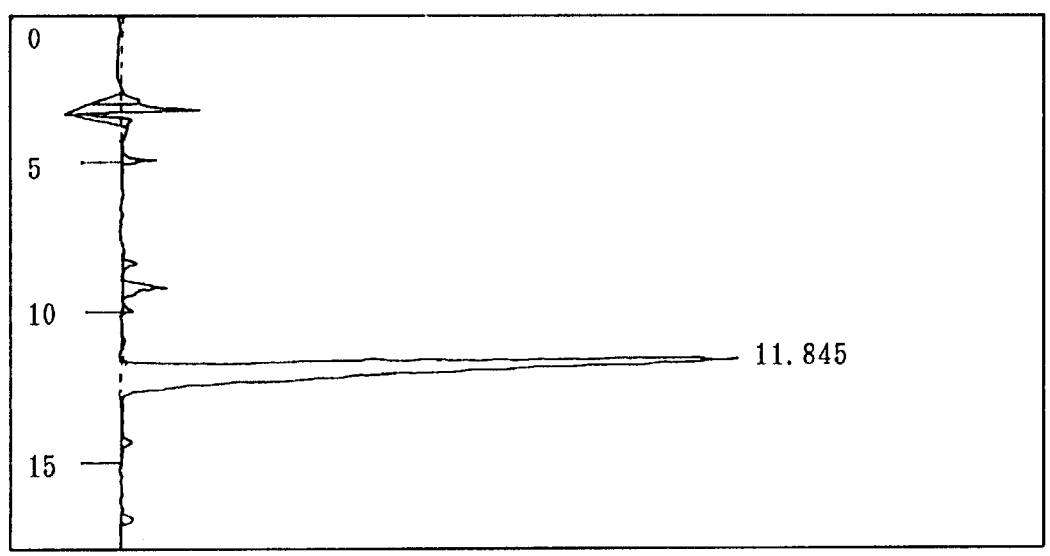
FIG. 5 shows an HPLC elution pattern of the bioactive substance TKR1785-I. The ordinate represents retention time (min.) and the abscissa represents the relative intensity of ultraviolet absorption.

(7) Reversed phase high performance liquid chromatography: elution pattern as shown in FIG. 5.

Structural analysis based on the above characteristics revealed that TKR1785-I has the chemical structure of formula (I).

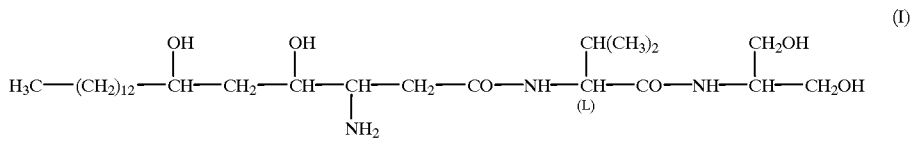

The bioactive substance TKR1785-II has the following physicochemical characteristics (8), (9), (10), and (11).

(8) Mass spectrum (FAB-MS): m/z 532 [M+H ]$^+$ (9) Molecular formula: C$_{28}$H$_{57}$N$_3$O

Figure 6:
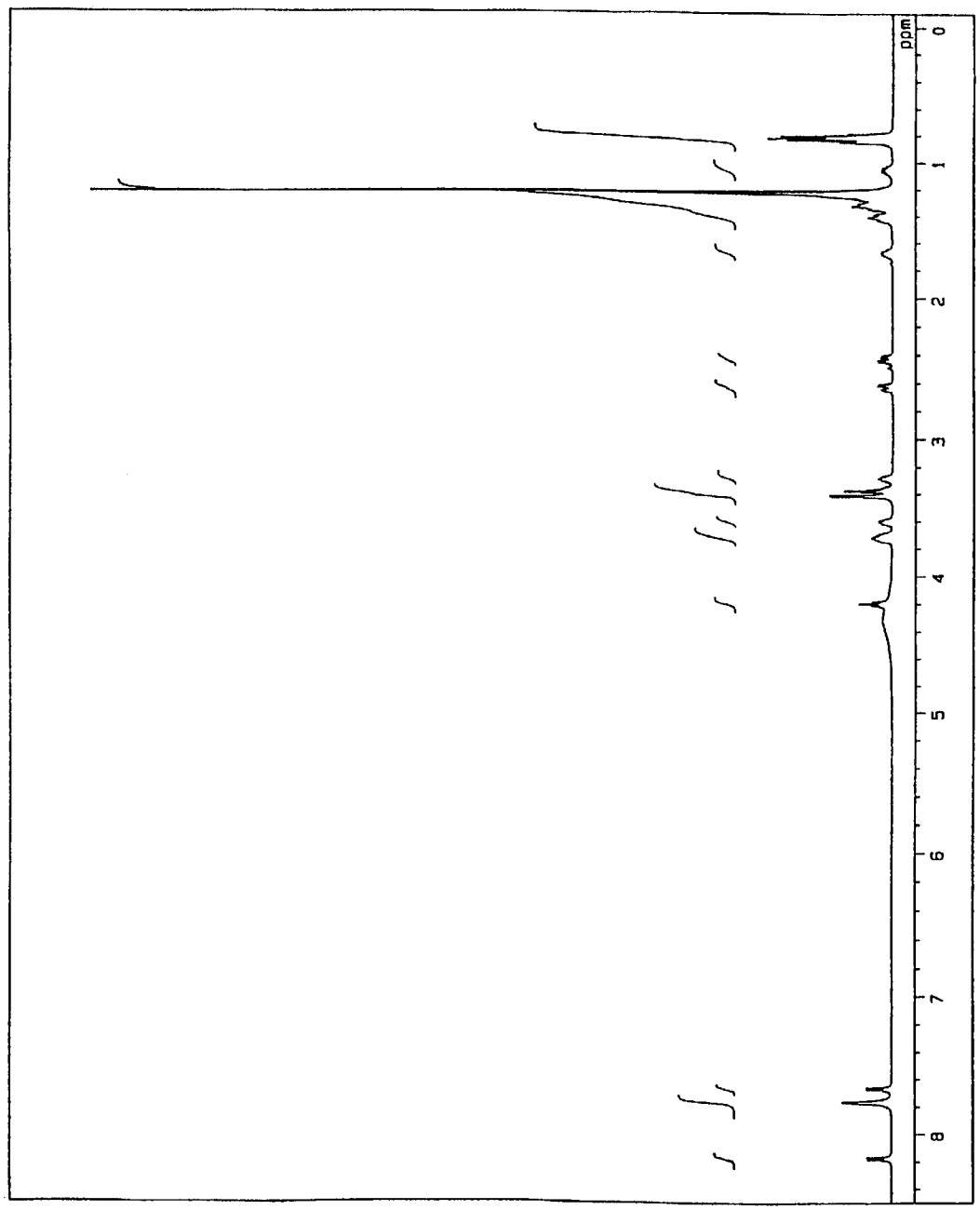
FIG. 6 is a $^1$H-NMR spectrum of the bioactive substance TKR1785-II. The abscissa represents chemical shift (ppm).
Figure 7:
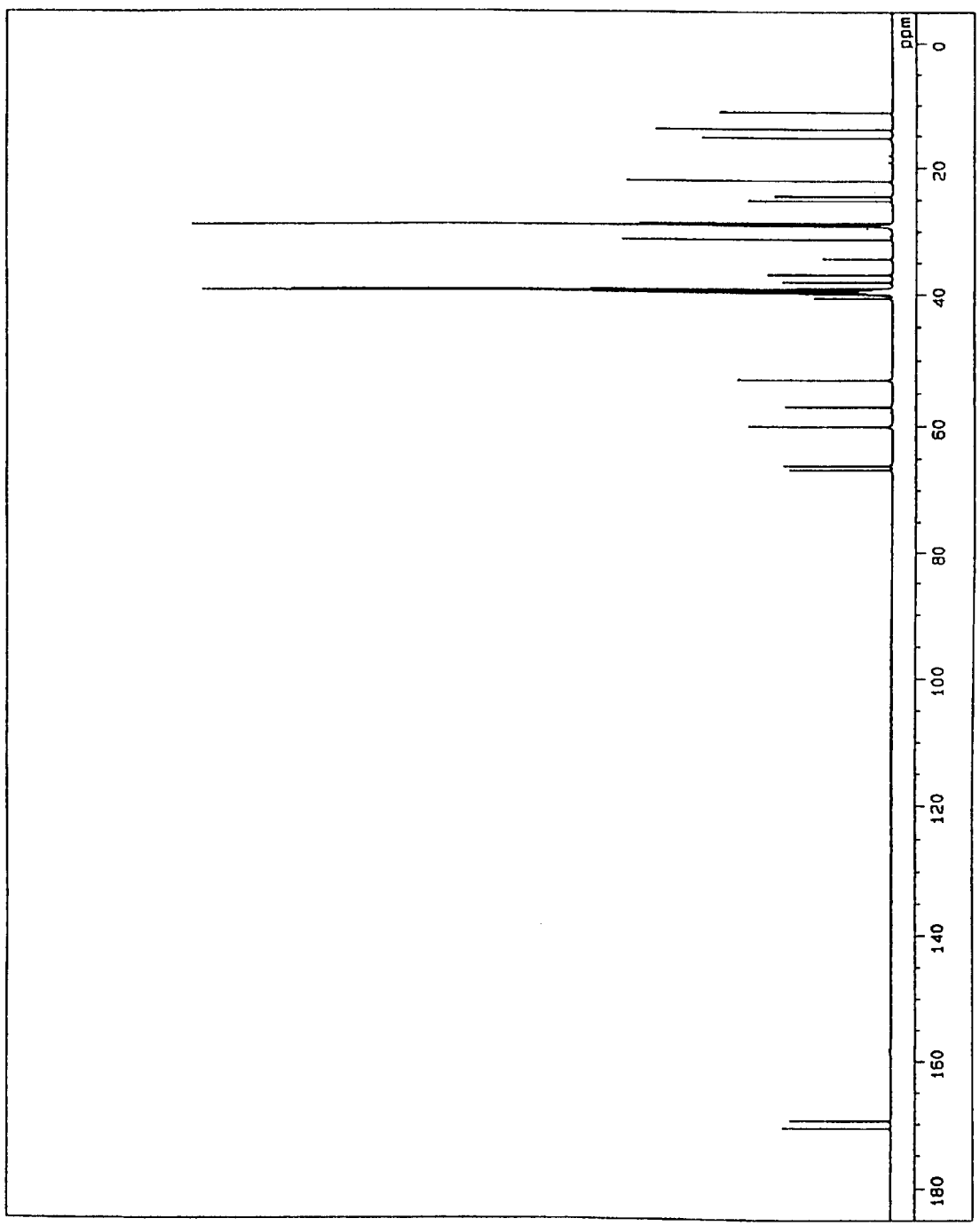
FIG. 7 is a $^{13}$C-NMR spectrum of the bioactive substance TKR1785-II. The abscissa represents chemical shift (ppm).

(10) $^1$H-NMR spectrum: FIG. 6 and $^{13}$C-NMR spectrum: FIG. 7.

Figure 8:
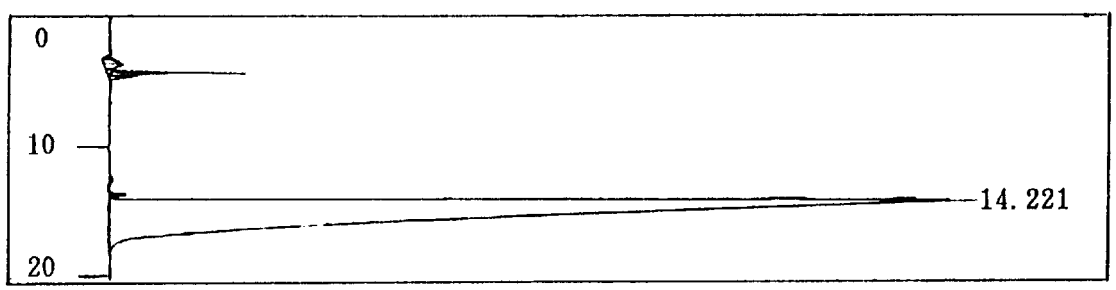
FIG. 8 shows an HPLC elution pattern of the bioactive substance TKR1785-II. The ordinate represents retention time (min.) and the abscissa represents the relative intensity of ultraviolet absorption.

(11) Reversed phase high performance liquid chromatography: elution pattern as shown in FIG. 8.

Structural analysis based on the above characteristics revealed that the bioactive substance TKR1785-II has the chemical structure of formula (II).

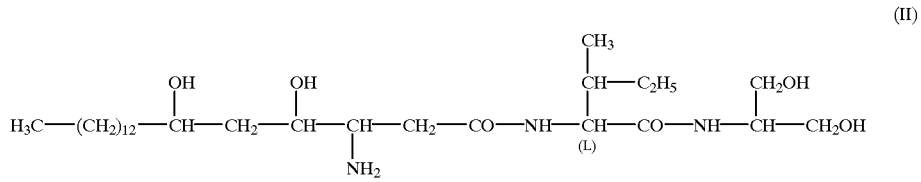

The above TKR1785 can be produced by culturing a strain of microorganism belonging to the genus Penicillium and capable of elaborating said TKR1785 and isolating said substance from the resulting culture broth.

The above-mentioned strain of microorganism is not particularly restricted provided that it belongs to the genus Penicillium and is capable of producing said TKR1785. Thus, for example, Penicillium sp. TKR1785 (hereinafter referred to as the TKR1785 strain) can be mentioned.

The TKR1785 strain is a novel fungal strain isolated from a sample collected in Hyogo Prefecture and characterized. It has the property to produce TKR1785 with good efficiency. The mycological characteristics of this TKR1785 strain are now described in detail.

The colony colors of the TKR1785 strain on various media are presented in Table 1. The color descriptions in the table are based on the color nomenclature defined in JIS Z 8102 (1985) and represent the results of observation after 7 days of culture at 25° C.

TABLE 1

| Medium | Colony diameter (mm) | Colony color | Surface color of the colony | Texture of the colony |
|---|---|---|---|---|
| Malt extract agar | 32 | Dark grayish yellow green 5GY4/2 | Grayish yellow green 10Y6/2 | Velvety |
| Potato dextrose agar | 29 | Dark grayish green 2.5G4/2 | Grayish yellow green 5GY6/2 | Velvety |
| Czapek's agar | 29 | Grayish green 10G5/2 | Greenish gray 5GY6/1 | Velvety |
| Sabouraud's agar | 40 | Dark grayish green 10GY4/3 | Grayish yellow green 5GY6/2 | Velvety |
| YpSs agar | 25 | Grayish yellow green 5GY6/2 | Dull yellow 2.5Y8/4 | Deeply Velvety |

The TKR1785 strain cultures rapidly on malt extract agar, potato dextrose agar, and Czapek's agar, giving colonies showing a velvety surface texture and a slightly elevated center. The conidiophore of the TKR1785 strain measures 90 to 270×1.8 to 3.0 $\mu$m and has a glabrous surface, usually forming symmetrically bivertillate penicilli. The metula measures 12.0 to 14.0×2.8 to 3.2 $\mu$m, occurring in groups of 2 to 4, and the phialides are whorled and sized 9.0 to 10.0×1.8 to 2.4 $\mu$m. The conidia are globose to subglobose, each having a glabrous surface and measuring 2.2 to 3.2×2.4 to 4.0 $\mu$m.

Among the mycological characters of the TKR1785 strain, its physiological characteristics are as follows.

Temperature range for growth: The temperature range for growth is 10 to 30° C. and the optimum range of temperature for growth is about 25° C.

The pH range for growth: The pH range for growth is pH 3 to 9 and the optimum range of temperature for growth is pH about 5.

When the above mycological characters are compared with the descriptions of Penicillium species in Carlos Ramirez, Manual and Atlas of the Penicillia, Elsevier Biomedical Press, 1982, among other literature, the TKR1785 strain can be identified to be a strain belonging to the genus Penicillium.

However, no report was available on a strain of microorganism having the ability to produce TKR1785 among fungi of the genus Penicillium. Therefore, the inventors of the present invention regarded it as a novel strain and named Penicillium sp. TKR1785. The strain was deposited with National Institute of Bioscience and Human Technology (Address, 1–3, Higashi 1-chome, Tsukuba-shi, Ibaraki, Japan (Zip code 305)) under the accession number of FERM BP-5788 (original date of deposit: May 17, 1995; date of request for transfer to international deposit: Jan. 17, 1997).

In the practice of the invention, not only the above TKR1785 strain but also spontaneous or artificial mutants of the TKR1785 strain as well as other strains of the genus Penicillium which are capable of producing TKR1785 can be employed with success.

The efficiency of production of the bioactive substance TKR1785 by the above-mentioned microorganism in a suitable culture system can be easily determined by the way of applying reversed phase partition high performance liquid chromatograph using the same conditions as used for generating the data plotted in FIG. 5 for confirming the elution position, measuring ultraviolet absorption spectrometry with a photodiode array or the like device, comparison of the physicochemical properties of the product with those mentioned for TKR1785, and where necessary, measuring molecular weight of the eluate from the reversed phase partition high performance liquid chromatograph with a reasonable molecular-mass measuring apparatus.

In accordance with the invention, TKR1785 can be produced by inoculating a nutrient medium with said TKR1785-producing strain of microorganism and incubating the inoculated medium. Referring to the nutrients which can be used, the carbon source includes but is not limited to glucose, fructose, saccharose, starch, dextrin, glycerin, molasses, malt syrup, oils, and organic acids.

The nitrogen source, among said nutrients, includes but is not limited to soybean flour, cottonseed flour, corn steep liquor, casein, peptone, yeast extract, meat extract, germs, organic or inorganic nitrogeneous compounds such as urea, amino acids, and ammonium salts. The salt, which is also among said nutrients, includes inorganic salts such as salts of sodium, potassium, calcium, magnesium, and phosphates. Those nutrients may respectively be used each independently or in a suitable combination.

Where necessary, the above nutrient medium may be supplemented with heavy metals such as iron salts, copper salts, zinc salts, cobalt salts, etc., vitamins such as biotin, vitamin $B_1$, etc., and other organic or inorganic substances for assisting in the growth of the microorganism and promoting the production of TKR1785.

Where necessary, the nutrient medium may be further supplemented with an antifoam or a surfactant, such as silicone oil, polyalkylene glycol ethers, and the like.

Cultivation of said TKR1785-producing strain in the above nutrient medium can be carried out by the routine cultural technology for incubating microorganisms for the production of bioactive substances. Preferred is a liquid cultural method, particularly shake culture or submerged aerobic culture.

The cultivation is preferably carried out in the temperature range of 15 to 25° C., and the pH of the medium is generally pH 3 to 8 and preferably about pH 5. A sufficient output can be expected generally within 3 to 11 days of culture.

As the microorganism is thus cultivated, TKR1785 is accumulated in both the supernatant fraction and cellular fraction of the culture broth. In the present invention, the TKR1785 accumulated in the culture broth can be obtained by being separated from the broth by taking advantage of the physicochemical properties and biological characteristics of this bioactive substance and, where necessary, be further purified.

The above-mentioned separation can be accomplished by extracting the whole culture broth with a non-hydrophilic organic solvent such as ethyl acetate, butyl acetate, chloroform, butanol, or methyl isobutyl ketone. As an alternative, the broth can be fractionated into a supernatant and cells by filtration or centrifugation and the bioactive substance be then isolated from each of the supernatant and the cells.

Separation of TKR1785 from the culture broth can be achieved not only by the above extraction procedure using a non-hydrophilic organic solvent but also by the procedure which comprises contacting the broth with an adsorbent stationary phase to let TKR1785 adsorbed and eluting the bioactive substances from the stationary phase with a solvent. The stationary phase includes but is not limited to activated carbon, cellulose powder, and adsorbent resin and the like. The solvent can be used either singly or in a combination of two or more species according to the type and properties of the stationary phase selected. Thus, for example, aqueous solutions of water-soluble organic solvents, such as aqueous acetone and aqueous alcohols can be used. For separation of TKR1785 from the cells, an extraction procedure using a hydrophilic organic solvent such as acetone may for example be used.

In the present invention, a crude extract of TKR1785 thus separated from the culture broth can be further purified as desired. This purification can be carried out by the technology used generally in the separation and purification of lipid-soluble bioactive substances, for example by column chromatography or high performance liquid chromatography using such a stationary phase such as silica gel, activated alumina, activated carbon, or adsorbent resin. The eluent for use in silica gel column chromatography, for instance, includes chloroform, ethyl acetate, methanol, acetone, and water, among other solvents, and those solvents can be used each alone or in combination.

In the case of high performance liquid chromatography, the stationary phase that can be used includes but is not limited to chemically bonded silica gels such as octadecylated, octylated, or phenylated silica gels and polystyrene series porous polymer gels. As the mobile phase, aqueous solutions of water-soluble organic solvents such as aqueous methanol, aqueous acetonitrile, etc. can be used.

TKR1785 according to the invention can be used in medicinal applications, either as it is or in the form of a pharmacologically acceptable salt. The pharmaceutical composition comprising TKR1785 or a pharmacologically acceptable salt thereof is not particularly restricted but includes antifungal, antiallergic, and immunomodulators. Although antiallergic and/or immunomodulators are preferred applications of the invention, the scope of applicability of the invention is not limited to such uses but all kinds of medicinal compositions comprising TKR1785 or its pharmacologically acceptable salt, even if intended for other applications, fall within the scope of the invention.

The salt mentioned above is not particularly restricted provided that it is pharmacologically acceptable. Thus, the salt includes but is not limited to salts with mineral acids such as hydrochloric acid, sulfuric acid, nitric acid, phosphoric acid, hydrofluoric acid, hydrobromic acid, etc.; salts with organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc.; and salts with alkali metals or alkaline earth metals such as sodium, potassium, and calcium.

TKR1785 or its pharmacologically acceptable salt according to the invention can be administered either as it is or in the form of a pharmaceutical composition containing it in a proportion of 0.1 to 99.5%, preferably 0.5 to 90%, in a pharmaceutically acceptable, nontoxic and inert excipient, typically as an antifungal, an antiallergic agent or an immunomodulator, to animals including men.

The excipient mentioned above includes solid, semi-solid, or liquid diluents, fillers, and other formulating auxiliaries and those substances can be used either singly or in combination.

The above pharmaceutical composition is preferably administered in unit dosage forms and can be administered orally, parenterally, locally (e.g. transdermally), or rectally. Of course, the above-mentioned pharmaceutical composition is administered in dosage forms suited to respective routes of administration.

In the medicinal application of TKR1785 or its pharmacologically acceptable salt according to the invention, the dosage as an antifungal, an antiallergic, or an immunomodulator, is preferably adjusted according to patient factors such as age and body weight, the route of administration, and the nature and severity of illness, among other factors, but the usual daily dosage for an adult patient is 10 to 2000 mg as the active ingredient, namely TKR1785 or a pharmacologically acceptable salt thereof. Whereas doses below the above-mentioned range may be sufficient in certain cases, higher doses may be needed in other cases. In high-dose administration, the daily dosage is preferably administered in several divided doses.

The oral administration can be made in solid, powdery, or liquid unit dosage forms such as bulk powders, powders, tablets, dragees, capsules, drops, and sublingual tablets, among other dosage forms. For example, bulk powders can be manufactured by comminuting TKR1785 or its pharmacologically acceptable salt of the invention into a finely divided form. The above-mentioned powders can be manufactured by comminuting TKR1785 or its pharmacologically acceptable salt into a finely divided form and blending the resulting powder with a similarly comminuted pharmaceutical excipient, e.g. an edible carbohydrate such as starch, mannitol, or the like. Where necessary, a corrigent, preservative, dispersant, coloring agent, perfume, and/or other additive may also be formulated.

The parenteral administration can be made by using liquid dosage form, for example, a solution or suspension for subcutaneous, intramuscular, or intravenous administration, among other forms. Those dosage forms can be manufactured by suspending or dissolving a predetermined amount of TKR1785 or its pharmacologically acceptable salt of the invention in a nontoxic liquid vehicle suited for injection of an aqueous or oily medium or the like, and sterilizing the suspension or solution.

The local administration (e.g. transdermal administration) can be made using external dosage forms such as a liquid, cream, powder, paste, gel, or ointment. Those dosage forms can be manufactured by formulating a predetermined amount of TKR1785 or its pharmacologically acceptable salt of the invention with at least one topical formulating agent selected from among a perfume, coloring agent, filler, surfactant, humectant, emolient, gelling agent, support, preservative, stabilizer, and so on.

The rectal administration can be made using suppositories prepared by mixing a predetermined amount of TKR1785 or its pharmacologically acceptable salt of the invention into a low-melting solid base, e.g. a higher ester such as myristyl palmitate ester, polyethylene glycol, cacao butter, or a mixture thereof.

BEST MODE FOR CARRYING OUT THE INVENTION

The following examples illustrate the present invention in further detail but are not intended to define the scope of the invention.

EXAMPLE 1

From a slant culture of TKR1785 strain (FERM BP-5788), a loop was taken to inoculate a 500 ml conical flask containing 100 ml of a liquid medium [Difco yeast nitrogen base 0.67% (w/v) and glucose 2.0% (w/v)] and cultured under shaking at 25° C. for 5 days to provide a seed culture. A 1.0 ml portion of this seed culture was inoculated into 18 conical flasks of 500 ml capacity each containing 125 ml of the above liquid medium and cultured under shaking (220 rpm) at 25° C. for 9 days. The resulting culture was centrifuged to separate a supernatant and a cellular fraction from each other. The cellular fraction was well mixed and extracted with 1 L of methanol and the extract was concentrated under reduced pressure. The residue was diluted with 300 ml of water and, after sufficient mixing, adjusted to pH 2. Then, 300 ml of ethyl acetate was added and mixed thoroughly for washing. The aqueous layer was adjusted to pH 9 and extracted with 300 ml of ethyl acetate. The extract was concentrated under reduced pressure to provide 52 mg of a residue.

This residue was dissolved in 0.4 ml of methanol and subjected to high performance liquid chromatography to provide two antifungal fractions I and II. Those active fractions were respectively concentrated under reduced pressure to provide 16 mg of TKR1785-I and 3 mg of TKR1785-II both as white powders. The high performance liquid chromatography was carried out under the following conditions.
Apparatus: LC8A (Shimadzu)
Column: YMCpack $C_{18}$ (2.0 cm×25 cm) (Y.M.C.)
Mobile phase: 0.05% trifluoroacetic acid-55% (v/v) acetonitrile/water
Physicochemical properties JMS-DX302 Mass Spectrometer (Jeol Ltd.) was used for mass spectrometry. JNM-A500 Nuclear Magnetic Resonance Spectrometer (Jeol Ltd.) was used for $^1$H-NMR spectrometry (in deuterated dimethyl sulfoxide; reference: deuterated dimethyl sulfoxide) and $^{13}$C-NMR spectrometry (in deuterated dimethyl sulfoxide; reference: deuterated dimethyl sulfoxide). For ultraviolet absorption spectrometry (in methanol), UV-250 self-recording spectrophotometer (Shimadzu) was used. For infrared absorption spectrometry (KBr), 270-30 Infrared Spectrophotometer (Hitachi) was used. L-8500 (Hitachi) was used for amino acid analysis.

The physicochemical properties of TKR1785-I are as follows.

Figure 2:
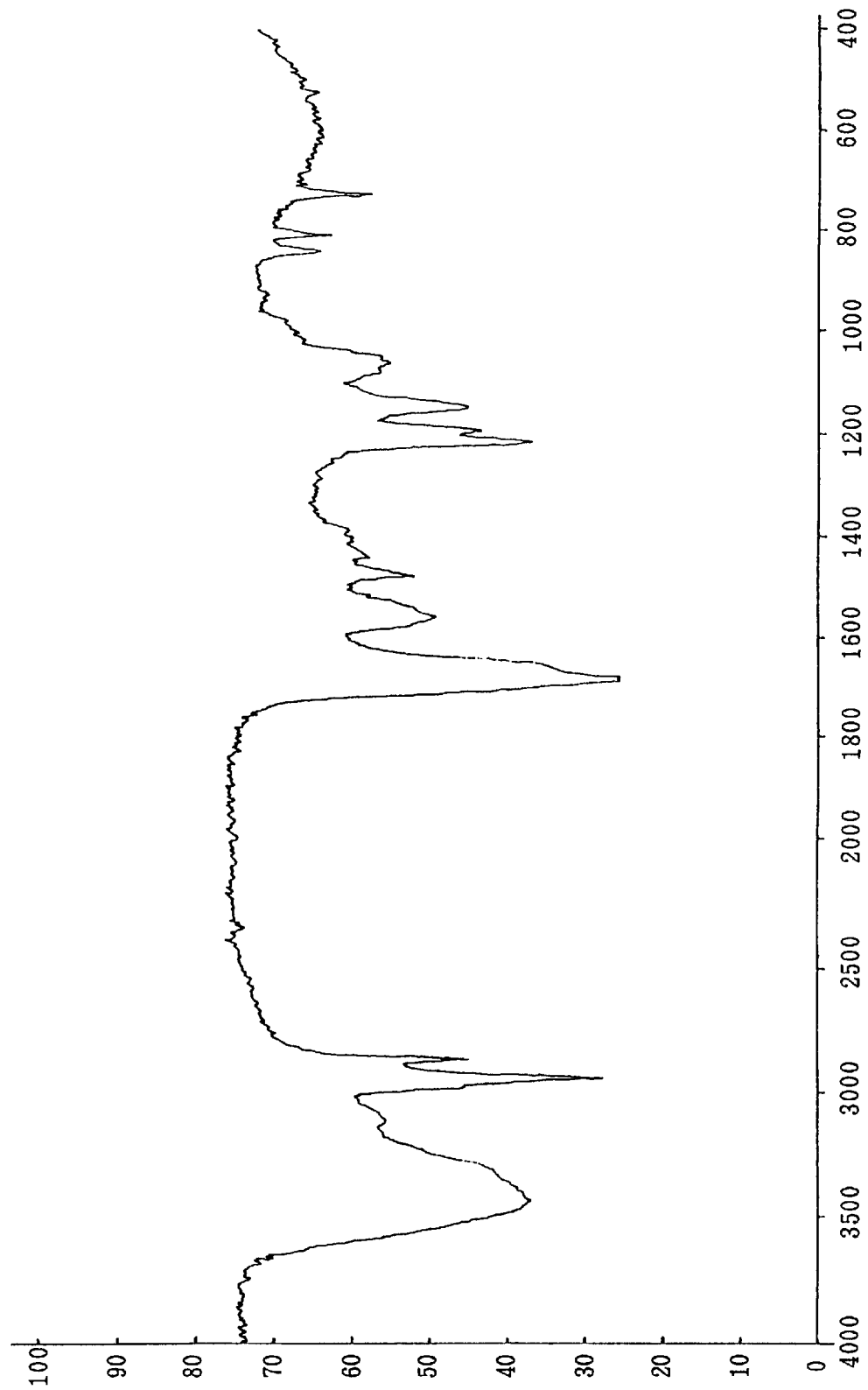
FIG. 2 is an infrared absorption spectrum of the bioactive substance TKR1785-I. The abscissa represents wavenumber (cm$^{-1}$).

FAB-MS of the purified white powder of fraction-I obtained by high performance liquid chromatography and concentration under reduced pressure shows m/z 518 [M+H]$^+$. Recording of $^1$H-NMR and $^{13}$C-NMR spectra and analysis thereof indicate that this substance has 27 carbon atoms and 3 nitrogen atoms. The $^1$H-NMR spectrum and $^{13}$C-NMR spectrum are presented in FIG. 3 and FIG. 4, respectively. The ultraviolet adsorption spectrum of this substance in methanol shows the terminal absorptions represented in FIG. 1. The KBr infrared absorption wavenumbers (KBr) are listed below. The IR absorption spectrum of the substance is presented in FIG. 2.
IR (KBr) (cm$^{-1}$): 3410, 2920, 2850, 1670, 1540, 1470, 1210, 1140, 1050, 840, 800, 720.

The solubility of this substance in various solvents was such that the substance is soluble in methanol and water and only sparingly soluble in chloroform and hexane.

The above analytical data revealed that the purified white powder obtained by high performance liquid chromatography and subsequent concentration of fraction I under reduced pressure is TKR1785-I. Detailed analysis of the $^1$H-NMR spectrum presented in FIG. 3 and the $^{13}$C-NMR spectrum presented in FIG. 4 revealed that TKR1785-I has the chemical structure of formula (I).

TKR1785-I was subjected to reversed phase partition high performance liquid chromatography (HPLC) using LC-10A High performance Liquid Chromatograph (Shimadzu). The high performance liquid chromatography was carried out under the following conditions.
Column: CAPCELL PACK $C_{18}$ (6 mm×150 mm) (Shiseido)
Mobile phase: 0.05% trifluoroacetic acid-50% (v/v) acetonitrile/water
Column temperature: 40° C.
Detection UV wavelength: 220 nm The analysis showed that TKR1785-I is eluted in the position indicated in FIG. 5.

The physicochemical constants of TKR1785-II are as follows.

The purified white powder obtained by high performance liquid chromatography and concentration of fraction II under reduced pressure was analyzed for various physicochemical properties. FAB-MS of this substance gave m/z532 [M+H]$^+$, indicating that it is larger than TKR1785-I by 14 mass units. This substance was hydrolyzed with hydrochloric acid and analyzed for amino acids. As a result, it was found that whereas TKR1785-I contains L-valine, this substance contains L-isoleucine. There was little difference between the UV absorption spectra of the two substances. The solubility of this substance in various solvents was also similar to that of TKR1785-I. Global analysis of the $^1$H-NMR spectrum (FIG. 6) and $^{13}$C-NMR spectrum (FIG. 7) of this substance revealed that the substance has the chemical structure of formula (II).

Based on the above analytical data, the purified white powder obtained by high performance liquid chromatography and concentration of active fraction II under reduced pressure was found to be TKR1785-II.

TKR1785-II was subjected to HPLC analysis using LC-10A High performance Liquid Chromatograph (Shimadzu). The HPLC conditions were the same as those used in the analysis or TKR1785-I. The analysis revealed that TKR1785-II was eluted in the position indicated in FIG. 8.
Biological Properties
(1) Antifungal activity The antifungal activity of the above substance TKR1785 against various microorganisms was investigated. Using the liquid medium dilution method, the concentration which caused substantially complete Inhibition of growth was determined as minimal inhibitory concentration ($\mu$g/ml). The results are presented in Table 2. The concentration causing a partial inhibition of growth was also determined as 50% inhibitory concentration ($\mu$g/ml) and is shown in parentheses of table 2. In the table, YNBG represents a medium containing 0.67% of yeast nitrogen base (Difco) and 1% of glucose. BHI represents a medium containing 0.5% of brain heart infusion bouillon (Nissui Pharmaceutical). YNBG-Tween represents a medium containing 0.67% of yeast nitrogen base, 0.5% bactocasitone, 2% of glucose, and 1% of Tween 40.

TABLE 2

| Tester strain | Medium | Minimal inhibitory concentration ($\mu$g/ml) | |
| --- | --- | --- | --- |
| | | TKR1785-I | TKR1785-II |
| Candida albicans TIMM0136 | YNBG | 12.5 (6.25) | 12.5 (6.25) |
| Candida kefir TIMM0301 | YNBG | 6.25 | 12.5 (6.25) |

TABLE 2-continued

| Tester strain | Medium | Minimal inhibitory concentration (μg/ml) | |
|---|---|---|---|
| | | TKR1785-I | TKR1785-II |
| Cryptococcus neoformans TIMM0354 | YNBG | 6.25 (3.13) | 12.5 (6.25) |
| Aspargillus fumigatus TIMM1776 | BHI | 25 (3.13) | 50 (25) |
| Malassezia furfur TIMM2782 | YNBG-Tween | (12.5) | --* |

--*; not determined

It is apparent from the results in Table 2 that the bioactive substances TKR1785 of the invention have antifungal activity against pathogenic fungi such as *Candida albicans, Candida kefir, Cryptococcus neoformans,* and *Malassezia furfur.*

(2) Enzyme inhibitory activity

The inhibitory activity of TKR1785-I against phospholipase $A_2$ (derived from porcine pancreas) and leukotriene (LT) $C_4$ synthase (derived from the guinea-pig lung), which are enzymes related to the immune system, was determined. Phospholipase $A_2$ activity was assayed for a hexane extract under acidic conditions by determining the [$^{14}$C]palmitic acid released from [$^{14}$C]phosphatidylcholine. $LTC_4$ synthase activity was assayed by determining the yield of $LTC_4$ from $LTA_4$ by the RIA method. The results are shown in Table 3.

TABLE 3

| Enzyme | Test concentration (μg/ml) | Inhibition (%) |
|---|---|---|
| Phospholipase $A_2$ | 100 | 92 |
| Phospholipase $A_2$ | 10 | 33 |
| Leukotriene $C_4$ synthase | 300 | 98 |
| Leukotriene $C_4$ synthase | 30 | 21 |

TKR1785-I inhibited phospholipase $A_2$ and $LTC_4$ synthase, both of which are enzymes associated with allergic reactions.

(3) Mixed lymphocyte reaction (MLR) inhibitory activity

From C57BL/6 and BALB/c mice, the spleen was isolated and homogenized in a medium to provide a cell suspension. The cell suspension derived from C57BL/6 mice was passed through a nylon wool column to prepare a T cell-rich fraction (responder cells). The BALB/c-derived cell suspension was irradiated with X-rays to prepare stimulator cells. The responder cells and stimulator cells were mixed in a ratio of 1:1 and incubated in a $CO_2$ incubator for 4 days. Following addition of 3H-thymidine, the cells were further culturen overnight. The cells were then recovered and the amount of $^3$H-thymidine uptake was determined. The samples (500, 125, 31.2, and 7.8 μg/ml solutions of dimethyl sulfoxide diluted with the medium) were respectively added in a proportion of 0.5% at mixing the responder cells with the stimulator cells to final concentrations of 25 to 0.039 μg/ml. The inhibitory activity was determined by comparison with the 3H-thymidine uptake in the sample-free group. TKR1785-I showed concentration-dependent MLR-inhibitory activity and its 50% inhibitory concentration was 0.41 μg/ml.

It was, thus, clear that the substances are effective in suppressing allergic and other immune reactions.

(4) Toxicity

The TKR1785-I and TKR1785-II obtained were respectively administered to ICR mice intraperitoneally in a dose of 50 mg/kg but no toxic response was found.

Dosage Form Example 1

| TKR1785-I | 50 mg |
|---|---|
| Lactose | 46 mg |
| Corn starch | 20 mg |
| Low-substitution hydroxypropylcellulose | 8 mg |
| Hydroxypropylmethylcellulose | 5 mg |
| Magnesium stearate | 1 mg |
| Total | 130 mg |

The above components other than hydroxypropylmethylcellulose and magnesium stearate were evenly mixed and using an 8% (w/w) aqueous solution of hydroxypropylmethylcellulose as binder, the mixture was wet-granulated to provide a granulation for compression. Then, magnesium stearate was mixed with the granulation and using a tablet machine the whole composition was compressed into tablets for oral administration, each measuring 7 mm in diameter and weighing 130 mg.

Dosage Form Example 2

| TKR1785-I | 1 g |
|---|---|
| Absorptive ointment | 99 g |
| (listed in The Pharmacopoeia of Japan) Total | 100 g |

TKR1785-I was thoroughly kneaded with a small amount of absorptive ointment and, then, the remainder of the ointment was added gradually, followed by thorough kneading to provide a homogeneous ointment. This ointment was to be applied to the affected area 4 to 5 times daily.

INDUSTRIAL APPLICABILITY

According to the present invention, the bioactive substances TKR1785 of clinical value as, for example, therapeutic agents for fungal infections, allergic diseases and immune diseases as well as a method for its production can be provided.

What is claimed is:

1. The bioactive substance TKR1785 of the following generael formula (A) or a pharmacologically acceptable salt thereof:

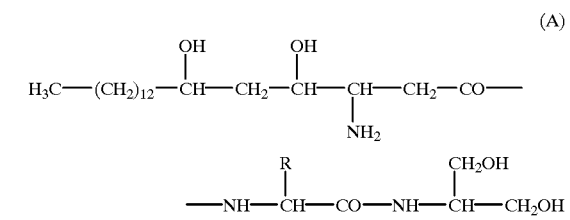

wherein R represents —$CH(CH_3)_2$ or —$CH(CH_3)C_2H_5$.

2. A method for treating an allergic disease which comprises administering the bioactive substance TKR1785 or a pharmacologically acceptable salt thereof as defined in claim 1 at an amount effective for treating said allergic disease.

3. A method for modulating an immune reaction which comprises administering the bioactive substance TKR1785 or a pharmacologically acceptable salt thereof as defined in claim 1 at an amount effective for modulating an immune reaction.

4. A method for inhibiting growth of fungus which comprises administering the bioactive substance TKR 1785 or a pharmaceutically acceptable salt thereof as defined in claim 1 at an antifungal effective amount.

5. A pharmaceutical composition comprising the bioactive substance TKR1785 or a pharmacologically acceptable salt thereof.

6. A method of producing the bioactive substance TKR1785 which comprises culturing a strain of microorganism belonging to the genus Penicillium and capable of producing the bioactive substance TKR1785 and isolating the substance from the resulting culture broth.

7. A microorganism belonging to the genus Penicillium and capable of producing the bioactive substance TKR1785.

* * * * *